United States Patent [19]

Nelson et al.

[11] Patent Number: 4,829,184

[45] Date of Patent: May 9, 1989

[54] REFLECTIVE, TRANSMISSIVE HIGH RESOLUTION IMAGING APPARATUS

[76] Inventors: Robert S. Nelson, 25511 El Conejo La., Laguna Hills, Calif. 92650; Reuven D. Zach, 27572 Santa Clarita Rd., Saugus, Calif. 91350

[21] Appl. No.: 22,283

[22] Filed: Mar. 5, 1987

Related U.S. Application Data

[63] Continuation-in-part of Ser. No. 624,467, Aug. 27, 1984, Pat. No. 4,649,275.

[51] Int. Cl.$^4$ .............. G01N 21/27; G01N 21/59
[52] U.S. Cl. .............. 250/358.1; 250/339; 250/341; 250/360.1; 128/664; 128/665
[58] Field of Search ........... 250/360.1, 358.1, 341, 250/339; 378/37; 128/665, 664

[56] References Cited

U.S. PATENT DOCUMENTS

| | | | |
|---|---|---|---|
| 4,481,418 | 11/1984 | Vanzetti et al. | 250/338 |
| 4,515,165 | 5/1985 | Carroll | 128/664 |
| 4,649,275 | 3/1987 | Nelson et al. | 250/358.1 |
| 4,699,149 | 10/1987 | Rice | 128/664 |

FOREIGN PATENT DOCUMENTS 2517129  6/1976  Fed. Rep. of Germany ...... 128/665

Primary Examiner—Janice A. Howell
Assistant Examiner—Constantine Hannaher
Attorney, Agent, or Firm—Lyon & Lyon

[57] ABSTRACT

A source of high resolution non-ionizing radiation of narrow spectral bandwidth is used in conjunction with optical detectors positioned on one or more sides of a breast to obtain mammographic images. Reflected and transmitted images may be obtained to determine the position of objects within the breast and their nature.

9 Claims, 5 Drawing Sheets

RASTER SCAN FORMAT INCIDENT NORMAL TO SURFACE

MULTIPLE RASTER SCAN

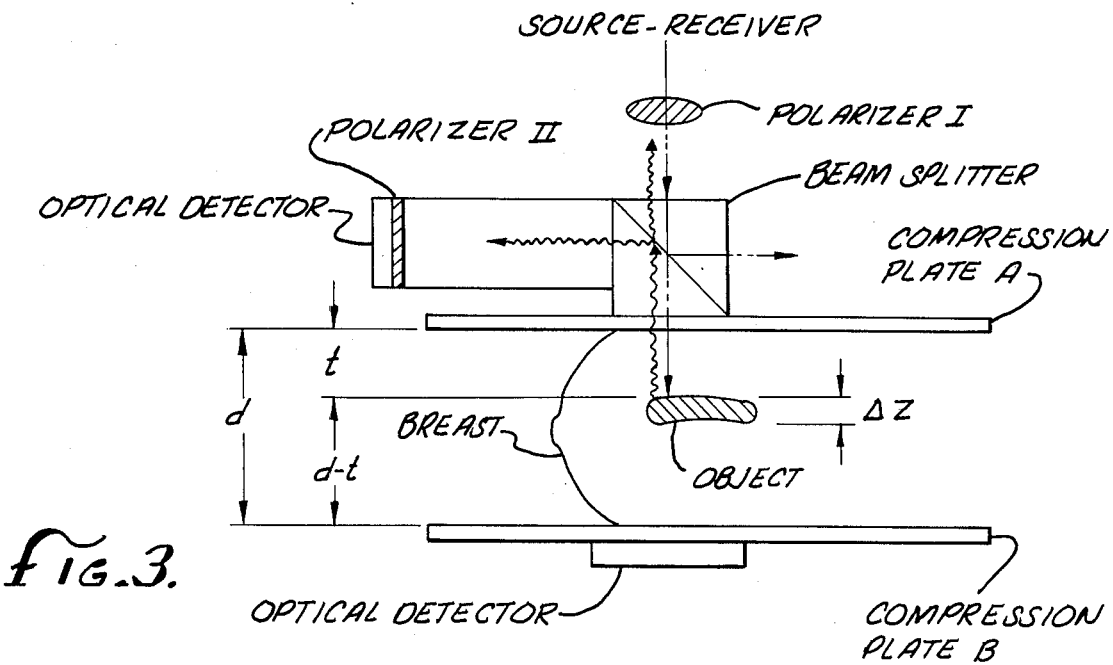
fig.3.
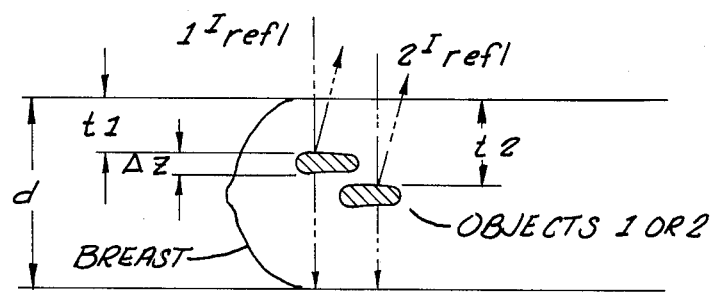
fig.4a.
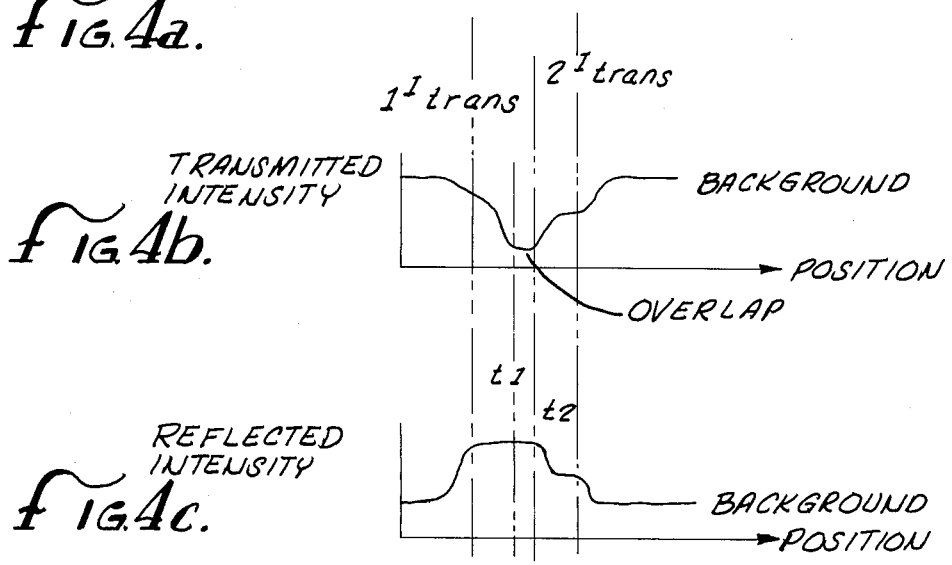
fig.4b.
fig.4c.

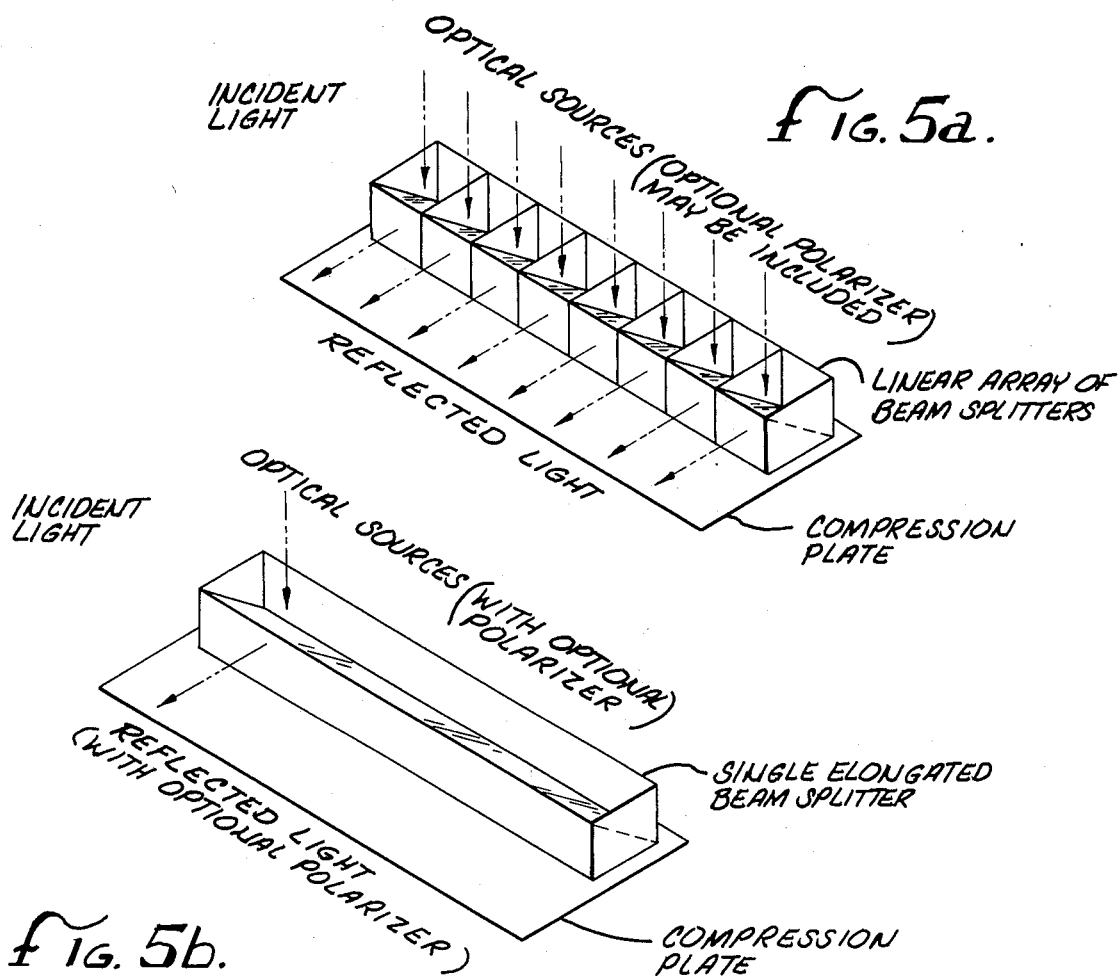
FIG. 5a.
FIG. 5b.
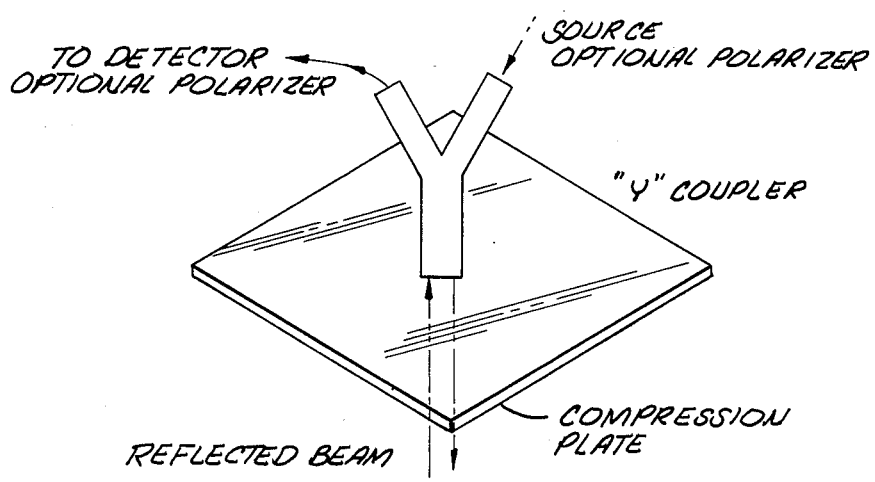
FIG. 6.

REFLECTIVE, TRANSMISSIVE HIGH RESOLUTION IMAGING APPARATUS

RELATED APPLICATIONS

This application is a continuation-in-part of Ser. No. 624,467 filed Aug. 27, 1984.

BACKGROUND OF THE INVENTION

X-ray mammography based on film-screen or xeroradiographic detection is commonly accepted as a mass screening technique for breast disease. However, certain risks are associated with x-ray examination because x-ray radiation is also ionizing. The possibility of genetic damage and radiation-induced cancer limits the recommended age group to older women as well as the frequency of exams.

More recently, broad beam light sources (sometimes referred to as "light torches") with a wide spectral bandwidth in the visible and infrared range have been used for breast imaging. The broad beam transmitted through the breast is usually recorded by a video camera, converted to an analog signal and viewed on a video monitor, or is digitized and analyzed on a computer. The ability to discriminate between various tissue-types in the breast, however, is reduced if the transmitted beam has a wide spectral bandwidth. Lesions which absorb, transmit, scatter, or reflect light to different degrees in comparison with normal tissue may exhibit reduced contrast. Moreover, the transmitted beam measurement includes the combined effects of absorption, reflection, and scattering. If a structure is highly reflective rather than strongly absorptive, the transmission measurement will not identify that property. It is thus very difficult to obtain information about the nature of the object, i.e., whether the object is a cyst, a tumor, a calcium deposit, etc.

Spatial resolution and contrast is also lost because a large amount of scattered light is transmitted from the breast to the detector. Also, structures nearest to the exit surface will cast more distinct shadows than objects close to the entrance surface. Lesion sizes that are detectable with this approach have generally been no smaller than what the physician can detect by palpation. Resolution is far below that which can be obtained with x-ray imaging systems.

Further limitations associated with measuring a transmitted beam are related to the position of objects along the beam path. Positional information of light attenuating objects is difficult to obtain because only the transmitted beam intensity is measured. If two objects obscure the beam, permitting only a weak beam to be transmitted, it is difficult to distinguish between them. Reversing the positions of the source and detector generates the same signal because the attenuating path remains the same. It is thus difficult to discern between one, two or more objects in the beam path.

SUMMARY OF THE INVENTION

The present invention is directed to a non-ionizing radiation imaging system for mammography. To this end, a source of non-ionizing radiation of narrow spectral bandwidth is used to produce a beam or a number of beams to be directed toward a breast. Optical detectors positioned on one or more sides of the breast are used to obtain high resolution images of radiation reflected from or transmitted through objects within the breast, or both. In this manner, improved image acquisition, object position and tissue-type data may be obtained.

BRIEF DESCRIPTION OF THE DRAWINGS

FIG. 3 shows an arrangement as in FIG. 1 for the imaging of reflected and transmitted light using a beam splitter. Polarizers are also shown adjacent the source and reflected radiation detector.

FIG. 4 (parts a, b and c) shows how transmitted and reflected imaging signals can be used to obtain positional information.

FIG. 5 (parts a and b) shows two beam splitter designs for use with a line radiation source.

FIG. 6 shows a fiber optic "Y" coupler for use in a one- or two-dimensional array.

DETAILED DESCRIPTION OF PREFERRED EMBODIMENTS

Figure 1A:
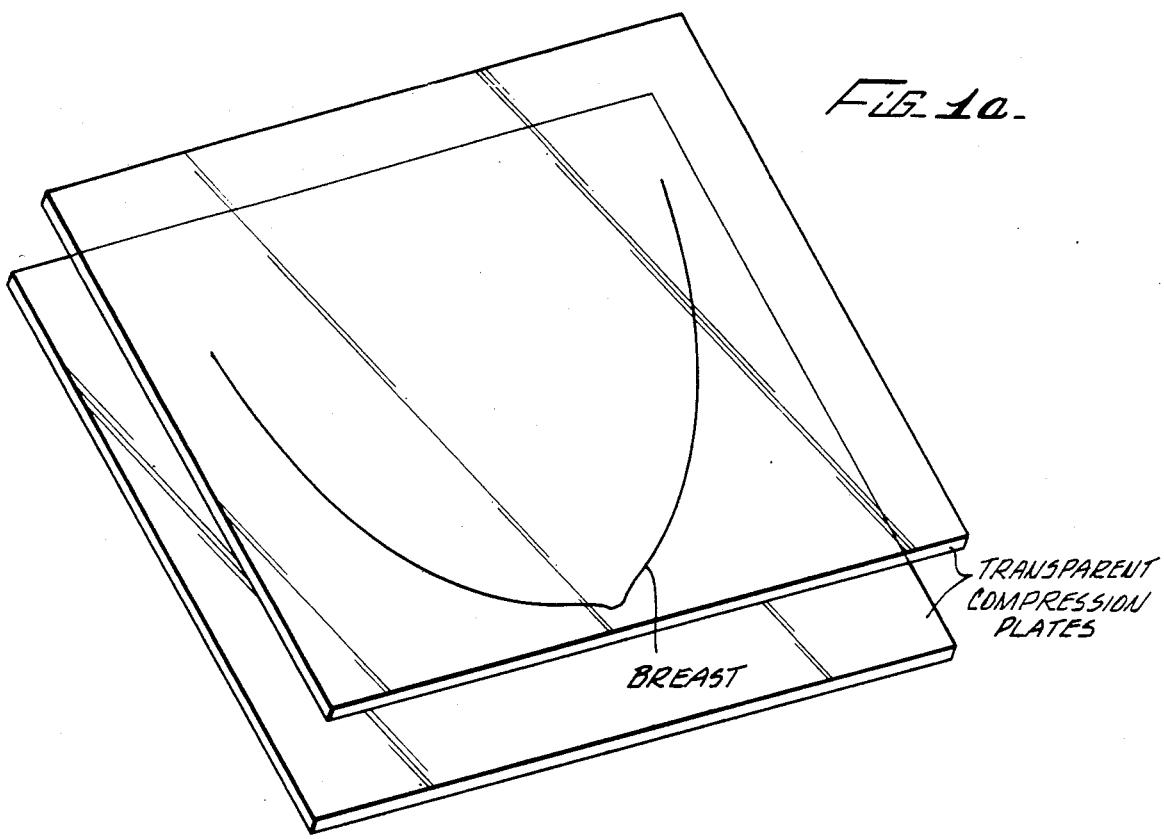
FIG. 1(a) shows a breast in a between two transparent plates. These "compression" plates are transparent to the light wavelengths which would be used in imaging the breast. For illustrative purposes, the size of these plates is similar to those used in conventional x-ray mammography. Plate size can be reduced to permit imaging of small sections of a breast.

FIGS. 1 and 2 depict apparatus for mammographic (breast imaging) applications which entail using light of narrow spectral bandwidth (near ultraviolet, visible or infrared) to obtain high resolution images. Appropriate narrow spectral bandwidth sources of light include lasers or filtered light sources. The light source is positioned on one side of the breast. A photodetector positioned on the opposite side of the breast records the transmitted light. Resolution is controlled by adjusting the cross sectional area of the light beam(s) before and-/or after transmission through the breast. Collimation introduced before the photodetector reduces the level of scattered light. The photodetector produces an analog signal which can be displayed or digitized for storage and analysis by a computer.

The breast often has an irregular shape. To reduce problems associated with light incident on and transmitted out of surfaces which are not necessarily normal to the direction of beam transmission, it is desirable to flatten the entrance and exit breast surfaces. This is easily accomplished using a pair of transparent flat compression plates. The optical path length can also be reduced by physically compressing the breast or a region thereof.

Figure 1B:
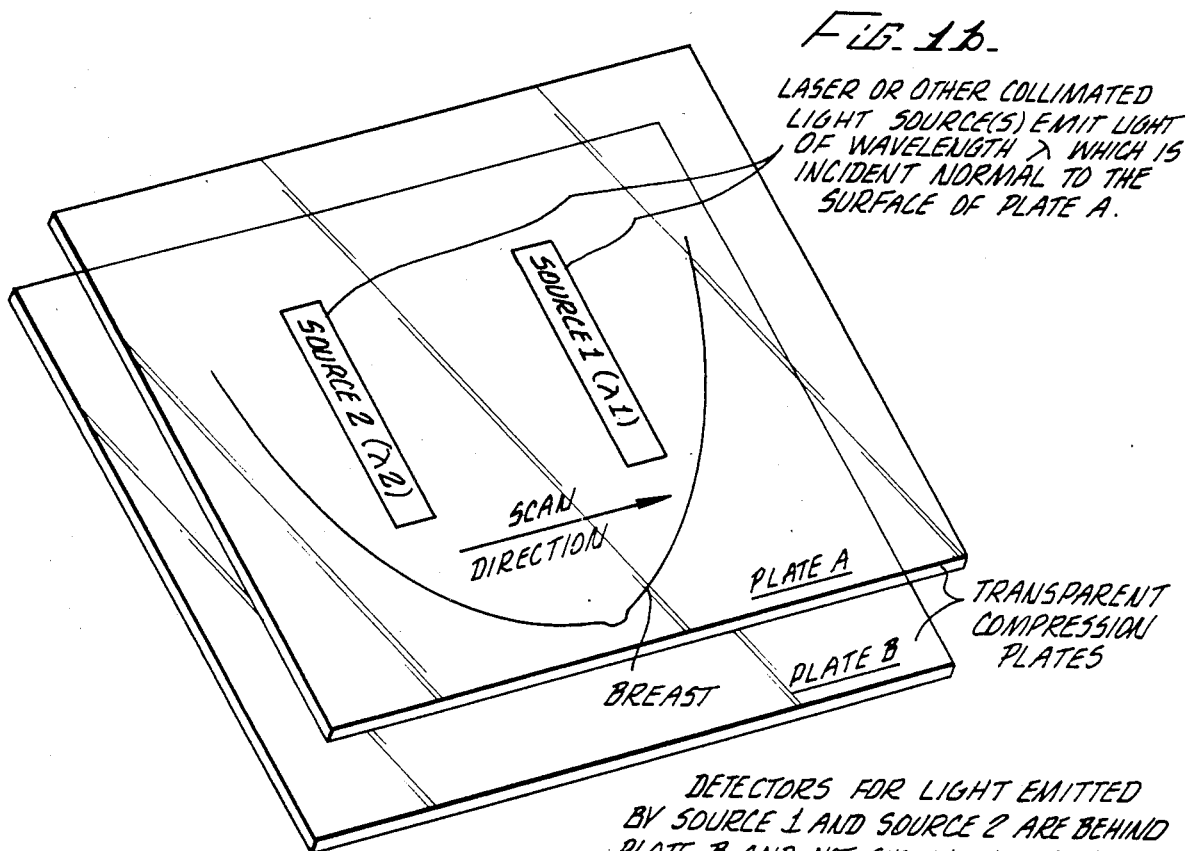
FIG. 1(b) shows the arrangement of FIG. 1 wherein one, two or more point, line or two-dimensional sources, each source emitting collimated light of a distinct wave length is (are) moved parallel to the surface of a compression plate. A detector corresponding to each source moves in synchronism with the source parallel to the surface of the second plate. Analog signals from the detector(s) can be digitized and stored in computer memory for display, processing and analysis purposes.

As can be appreciated from FIG. 1(b), light beams of wave length $\lambda_1$ and $\lambda_2$ sent from sources 1 and 2 are incident normal to the surface of one compression plate. The transmitted light is attenuated by the two plates and the breast material. An image or images can be acquired by simultaneously translating one or more plate source-light detector combinations past the breast. Each light source emits a different wavelength (e.g., $\lambda_1$ and $\lambda_2$ as shown in FIG. 1(b)).

Figure 2A:
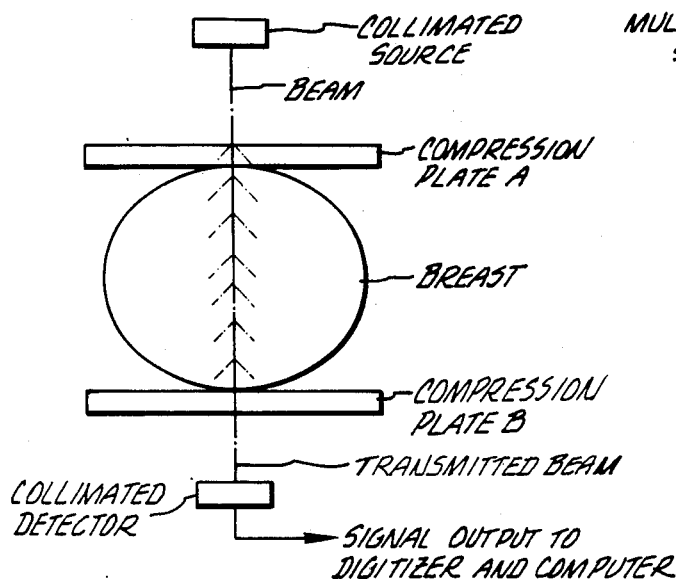
FIG. 2(a) shows a collimated pencil beam from a point source used in a raster format. The detector may use additional collimation to help minimize detection of scattered light. Collimation techniques for scatter reduction may include air-gaps, mechanical apertures such as grids, fiber optics or light pipes.
Figure 2B:
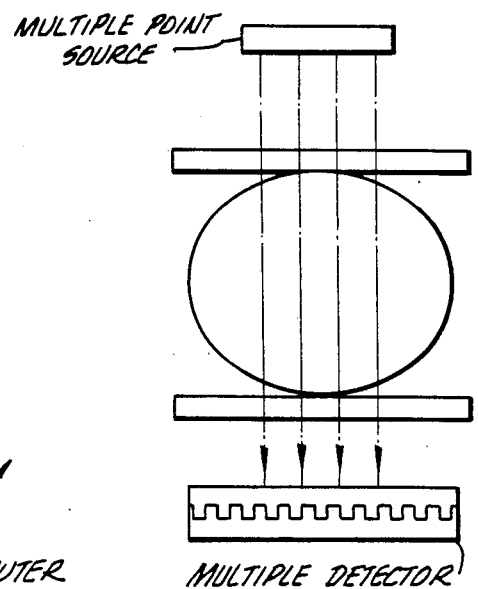
FIG. 2(b) shows multiple point beams used in a raster scan format to reduce image acquisition time.
Figure 2C:
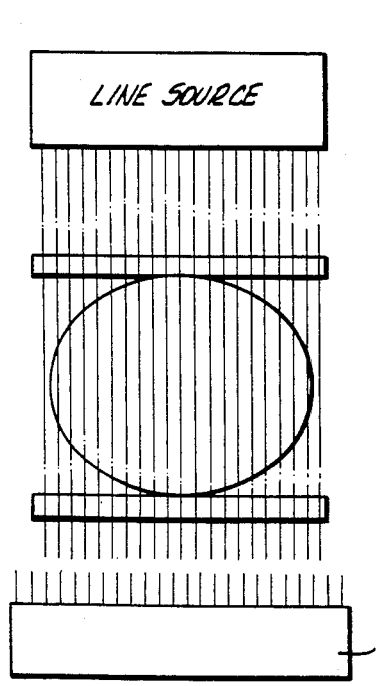
FIG. 2(c) shows a collimated (single or multiple) line beam of light providing a line scanning format. The array of detectors would use some form of collimation to reduce detected light scatter from the subject.

High resolution images may be obtained with a variety of scanning techniques. FIGS. 2(a) and (b) show a point beam or a multiple point beam which could be used in a raster scan format. The transmitted light beam can be collimated by a simple air gap, fiber optics, light pipes or mechanical apertures to minimize detection of scattered light. This approach can be extended to include a single line or a multiple line scanned format as shown in FIG. 2(c).

Figure 2D:
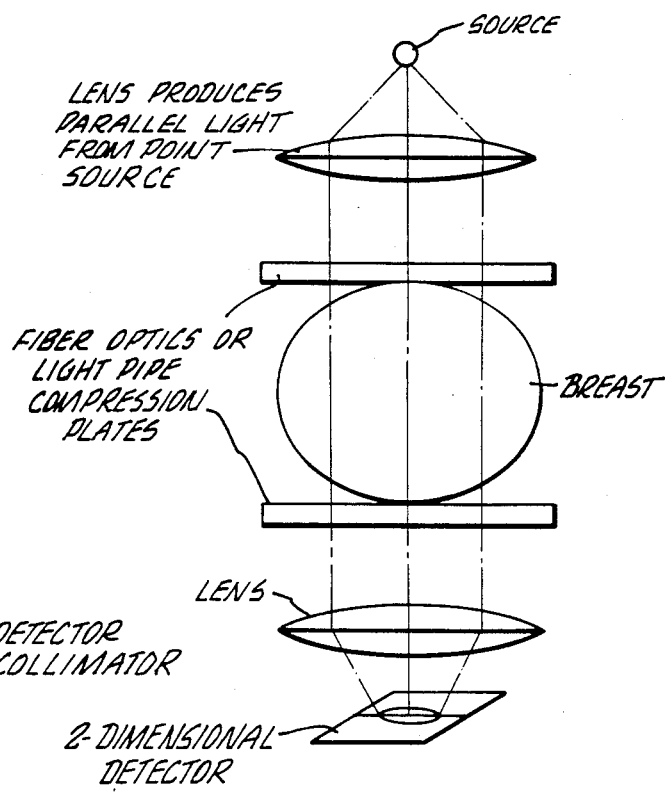
FIG. 2(d) shows a two-dimensional, parallel light beam used for rapid image acquisition by a two-dimensional detector. In this case, the collimation is incorporated into the compression plates.

High speed two-dimensional imaging is shown in FIG. 2(d). In this case, collimation (such as fiber-optics or light-pipes) can be introduced into one or both compression plates.

In all cases collimation may be used to produce a beam or beams of very small cross-section and a highly directional nature. This latter attribute can be used to exclude transmitted scatter from the exit beam. Since many versions of this invention are possible, light source requirements may range from a continuous to a rapidly pulsed source.

As shown in FIG. 3, an additional optical detector and a beam splitter may be positioned on the same side of the breast as the light source to form a source detector unit for recording light that is reflected from objects within the breast. In FIG. 3, the source-detector unit is disposed adjacent the top compression plate (plate A). The beam splitter, which is of conventional design, allows some fraction of the light from the source to pass into the breast. The optical detector placed beneath the bottom compression plate (plate B) will receive an image created by the transmitted light. Some fraction of the light which is reflected back from objects within the breast will be directed by the beam splitter to the optical detector measuring reflected light. The signals generate by each optical detector are directed to a computer for composite or separate image analysis.

Although not shown in FIG. 3, an alternative arrangement would be to replace the simple detector beneath the bottom compression plate with a second source-detector unit. By multiplexing the two source-detector units, the upper source-detector unit could be used to measure a reflected beam at one instance and then measure a transmitted beam at the next instance.

To prevent interference from light which is reflected back from the surface of the breast, it is advantageous, although not necessary, to employ a pair of polarizing filters I and II which are typically rotated 90° from each other. The first polarizer is placed adjacent to the source, while the second polarizer is placed adjacent to the reflective optical detector. Because light reflected from the breast surface would largely have a direction of polarization similar to that of the polarized input source, the second polarizer (which is a cross-polarizer when rotated 90° to the first polarizer) will attenuate such surface reflected light. It is also possible to rotate the second polarizer over a range of angles, thereby permitting the reflected light to be analyzed as a function of degree of rotation. If desired, the polarizers may be positioned directly on the beam splitter itself. Moreover, the first optical detector may likewise be mounted directly on the beam splitter.

Use of an optical detector to measure reflected light yields several advantages. First, high resolution images of objects located between the source side of the breast and the mid-point between the compression plates can be obtained due to the reduction in light path length and consequent decrease in attenuation and scatter. By obtaining images on opposite sides of the breast, most of the objects within the breast can be viewed with greater clarity. Second, a detector measuring the reflected beam can be used to obtain tissue-type data through determination of the reflective-transmissive properties of objects within the breast. Third, a detector measuring the reflected beam can be used to obtain positional information of objects within the breast.

FIG. 4 illustrates the above advantages. As shown therein, for objects having position $t < d/2$, a reflected image can be obtained using a total light path length that is less than d. The approximate z value of the object, which is the distance from the top compression plate to the object, can be determined, as can its reflectivity, if reflected images are obtained on opposite sides of the breast.

In FIG. 4, the z values for two objects 1 and 2 are designated $t_1$ and $t_2$, respectively. By directing a light source at opposite sides of the breast, the respective intensities of the reflected light can be measured. The measured intensity will relate to incident optical intensity in accordance with the following formula:

$$I_{refl} \sim I_0 Q e^{-2tu}$$

where:
- $I_{refl}$ = reflected optical intensity.
- $I_0$ = incident optical intensity at the entrance surface;
- t = actual depth of one surface of the object
- u = optical attenuation coefficient of breast medium;

If the thickness ($\Delta z$) of an object in the breast is small relative to breast thickness, i.e., $\Delta z << d$, the depth or z value of the object can be roughly estimated using the above equation. If Q and u remain the same for both measurements, and multiple reflections between the top and bottom surfaces of the object are ignored, then:

$$I_{refl}(\text{top}) \sim I_0 Q e^{-2tu} \text{ and}$$

$$I_{refl}(\text{bottom}) \sim I_0 Q e^{-2(d-t)u}$$

From these equations it is a simple matter of solving for the two unknowns t and Q to determine the z value and reflectivity of the object in question. If the object thickness, $\Delta Z$, is not small, then a third measurement using reflected or transmitted light, could be made at 90 degrees to the other measurements to determine $\Delta z$. In some cases a transmission measurement from one of the first two image scans may be useful in estimating Δz, or at least whether the object is thick or not (i.e. was the estimated attenuation by the object small or large for the type of object expected). Thus, if u' (optical attenuation coefficient of the object) is known, Δz could be estimated by introducing a third equation for the transmitted beam:

$$I_0[1-Q]e^{-(d-\Delta z)u - \Delta z u'}$$

while modifying $I_{refl}$ (bottom) $\sim I_0 Q e^{-2(d-t-\Delta z)u}$

The three equations may be solved to find Q, t and Δz.

If two objects partially obscure each other and are not too close together, two reflection measurements as described above can be of help in distinguishing the objects. There may be some edge enhancement at the position of overlap of objects 1 and 2 due to double reflection. The reflected intensity pattern would be roughly reversed if measurements were taken with the detector receiver units placed on the opposite side of the breast.

The beam splitter approach for detecting the reflected beam can be implemented in a linear or two-dimensional array as shown in FIG. 5. The reflected light passes through an optional polarizer, and is brought to an array of detectors (or a camera) with an optional polarizer by a collecting lens or light-pipes. Detectors can be mounted on the array directly. Mirrors can be introduced to alter the path further.

An alternative to the beam splitter arrangement shown in FIG. 5 is to use a fiber-optic "Y" coupler or fiber splitter with or without polarizers for the input and reflected signal as shown in FIG. 6. The reflected beam is directed to an optical detector. This can be utilized in a one- or two-dimensional array. The "Y" coupler is sometimes referred to as a "Y branch" coupler (see, IEEE Spectrum, p. 58 (March 1986)). Similarly, a directional coupler can be used to combine the source and reflected beams (Id. at 58).

Figure 7:
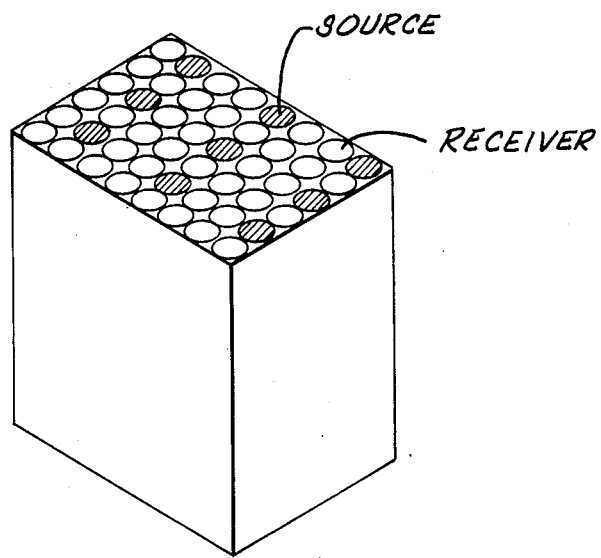
FIG. 7 shows a fiber bundle comprising source fibers (shaded) and receiver fibers.
Figure 8:
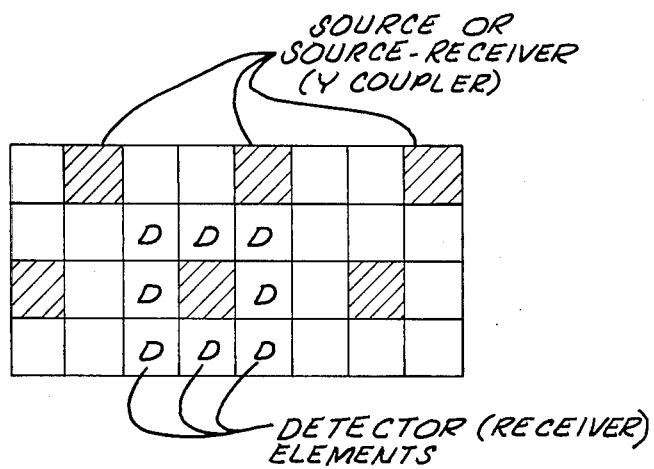
FIG. 8 shows a fiber arrangement format wherein each source fiber (which may also be a receiver fiber) is surrounded by receiver fibers to sample the reflected light.

When a two-dimensional (or linear) array is contemplated, several fibers (a bundle) may be incorporated into one radiation detecting element. As shown in FIG. 7, some fibers may be used as sources, while the other fibers are used as receivers. Polarizers may be used on the input and output. FIG. 8 shows a possible arrangement of source or source/receiver and receiver fibers in a fiber bundle. In this arrangement, each source element has a plurality of nearest receiver fiber neighbors (in this case there are eight neighbors). The reflected light can be sampled by all eight neighbors or some subset thereof. The receiver fibers can all be coupled to independent optical detectors or to only one optical detector.

The idea of a beam splitter (Y couplers, etc.) can also be employed with a mask scanned format. The purpose of the mask is to minimize optical cross-talk between sources by ensuring adequate spatial separation between those sources. The mask moves in order to sample all points on the compression plate. If a two-dimensional source is used to illuminate a strip or an entire area, a mask with opaque areas will be needed. A virtual mask can be constructed with fiber-optics by spatially separating the source fibers. The described reflection imaging devices can be incorporated into an optical CT scanner. Transmission CT images, reflection CT images, and composite CT image (using information from the first two images) could be reconstructed.

Thus, a reflective/transmissive high resolution imaging apparatus is disclosed. Reflected and transmitted light may be imaged for a variety of purposes including tissue identification and determination of an object's relative z value. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. An apparatus for obtaining tissue images using non-ionizing radiation, comprising:
   a source of non-ionizing radiation of relatively narrow bandwidth disposed such that radiation will be incident on a first side of the tissue to be scanned;
   an optical detector disposed on the first side of the tissue to be scanned for detecting radiation that is reflected from objects within the tissue; and
   means for collimating said radiation into one or more beams of highly directional nature such that the radiation components of said beam or beams all have substantially parallel direction vectors.

2. The apparatus set forth in claim 1 further including a beam splitter disposed between said radiation source and said tissue to pass radiation incident from said source and reflect radiation reflected from objects within said tissue.

3. The apparatus set forth in claim 2 wherein said beam splitter is a fiber optic "Y" coupler.

4. The apparatus set forth in claim 3 wherein said "Y" coupler contains source and receiver fibers, each of said source fibers having a plurality of receiver fiber neighbors.

5. The apparatus set forth in claim 1 further including a first polarizer positioned adjacent said radiation source and a second polarizer positioned adjacent said optical detector, said polarizers being oriented to reduce the intensity of radiation reflected from said tissue on said optical detector.

6. An apparatus for obtaining tissue images using non-ionizing radiation, comprising:
   a source of non-ionizing radiation of relatively narrow bandwidth disposed such that radiation will be incident on a first side of a tissue;
   a first optical detector disposed on the first side of the tissue for detecting radiation that is reflected from objects within the tissue;
   a second optical detector disposed on a second side of the tissue for detecting radiation that passes through the tissue; and
   means for collimating said radiation into one or more beams of highly directional nature such that the radiation components of said beam or beams all have substantially parallel direction vectors.

7. The apparatus set forth in claim 6 further including a source of non-ionizing radiation of relatively narrow bandwidth disposed such that radiation will be incident on the second side of the tissue, and means for collimating said radiation incident on the second side of the tissue into one or more beams of a highly directional nature.

8. A method for determining the relative z-value and/or reflectivity of objects disposed in a breast comprising the steps of:
   irradiating a first side of a breast with non-ionizing radiation of relatively narrow bandwidth, detecting the radiation that is reflected from objects in the breast and measuring the intensity of the reflected radiation;

irradiating a second side of the breast opposite from the first side of the breast, detecting the radiation that is reflected from objects in the breast and measuring the intensity of the reflected radiation; and comparing the relative intensities of the reflected radiation detected on each side of the breast.

9. A method for determining the relative z value and/or reflectivity of objects disposed in a tissue comprising the steps of:

irradiating a first side of the tissue with non-ionizing radiation of relatively narrow bandwidth, detecting the radiation that is reflected from objects in the tissue and measuring the intensity of the reflected radiation;

irradiating a second side of the tissue opposite from the first side of the tissue, detecting the radiation that is reflected from objects in the tissue and measuring the intensity of the reflected radiation; and comparing the relative intensities of the reflected radiation detected on each side of the tissue.

* * * * *